US009514278B2

(12) United States Patent
Bahorich

(10) Patent No.: US 9,514,278 B2
(45) Date of Patent: Dec. 6, 2016

(54) DIAGNOSTICS METHOD BASED ON INPUT FROM MULTIPLE USERS

(71) Applicant: Michael S. Bahorich, Houston, TX (US)

(72) Inventor: Michael S. Bahorich, Houston, TX (US)

(*) Notice: Subject to any disclaimer, the term of this patent is extended or adjusted under 35 U.S.C. 154(b) by 93 days.

(21) Appl. No.: 14/153,172

(22) Filed: Jan. 13, 2014

(65) Prior Publication Data

US 2014/0197947 A1 Jul. 17, 2014

Related U.S. Application Data

(60) Provisional application No. 61/751,970, filed on Jan. 14, 2013.

(51) Int. Cl.
| G08B 1/08 | (2006.01) |
| A61B 5/00 | (2006.01) |
| A61B 5/05 | (2006.01) |
| G06F 19/00 | (2011.01) |
| A61B 5/0205 | (2006.01) |

(52) U.S. Cl.
CPC ......... *G06F 19/3418* (2013.01); *A61B 5/0022* (2013.01); *A61B 5/0024* (2013.01); *A61B 5/02055* (2013.01); *A61B 5/6801* (2013.01); *A61B 5/6805* (2013.01); *A61B 2562/0242* (2013.01)

(58) Field of Classification Search
CPC ............. A61B 2562/0242; A61B 5/0022; A61B 5/0024; A61B 5/02055; A61B 5/6801; A61B 5/6805; G01R 31/2827; G01R 31/2829; G01R 31/3278; G06F 19/3418; G08C 17/02
USPC ............. 340/539.12, 539.11, 539.13, 539.1, 340/573.1; 600/301, 309, 388, 509; 709/217; 128/903
See application file for complete search history.

(56) References Cited

U.S. PATENT DOCUMENTS

| 6,280,380 | B1* | 8/2001 | Bardy | A61B 5/0002 600/300 |
| 6,428,475 | B1* | 8/2002 | Shen | A61B 5/0225 128/903 |
| 7,181,505 | B2* | 2/2007 | Haller | A61B 5/0031 607/32 |
| 7,751,873 | B2* | 7/2010 | de Voir | A61B 5/04017 600/509 |
| 7,978,062 | B2* | 7/2011 | Lalonde | A61N 1/37282 340/539.1 |
| 8,140,143 | B2* | 3/2012 | Picard et al. | 600/388 |
| 2007/0180047 | A1* | 8/2007 | Dong | A61B 5/0002 709/217 |
| 2010/0063365 | A1* | 3/2010 | Pisani | A61B 5/0002 600/301 |
| 2012/0130203 | A1* | 5/2012 | Stergiou | A61B 5/0002 600/301 |
| 2012/0136231 | A1* | 5/2012 | Markel | A61B 5/0015 600/388 |
| 2013/0307686 | A1* | 11/2013 | Frauenthal | A61B 5/746 340/539.12 |
| 2014/0206948 | A1* | 7/2014 | Romem | A61B 5/0022 600/301 |

* cited by examiner

*Primary Examiner* — Andrew Bee
*Assistant Examiner* — Munear Akki
(74) *Attorney, Agent, or Firm* — Richard A. Fagin

(57) ABSTRACT

A body function analysis and communication system includes a plurality of wireless communication devices each worn or carried by a respective user and in signal communication with an analysis system. Each wireless communication device is in signal communication with at least one sensor worn by the respective user. The analysis system is configured to determine anomalous response of measurements of the at least one sensor worn by at least one user based on measurements from the plurality of sensors.

10 Claims, 2 Drawing Sheets

DIAGNOSTICS METHOD BASED ON INPUT FROM MULTIPLE USERS

CROSS-REFERENCE TO RELATED APPLICATIONS

Priority is claimed from U.S. Provisional Application No. 61/751,970 filed on Jan. 14, 2013 and incorporated herein by reference in its entirety.

STATEMENT REGARDING FEDERALLY SPONSORED RESEARCH OR DEVELOPMENT

Not applicable.

BACKGROUND

This disclosure relates generally to the field of wearable sensors for measuring various vital signs of the wearers. More specifically, the disclosure relates to diagnostic methods using input from multiple wearable sensor users in communication with an analysis system.

Recently, various types of wrist wearable equivalents to so called "smart phones" have been developed. Examples include the SMARTWATCH brand device, which is a trademark of Sony Electronics, Inc. Another example is the MONOACTV brand device, which is a trademark of Motorola Mobility, Inc., USA. The foregoing devices may include some or all of the features available in currently available smart phones, including Internet browsing, voice communication, SMS text messaging and other programs (applications) commonly used in smart phones.

Another set of devices include a watch that can communicate with various body function sensors, sold under the trademark VESAG with is a registered trademark of Vyzin Inc. Sensors which may be embedded in the watch include accelerometers, and sensors which may communicate, e.g., by Bluetooth or similar wireless communication protocol may include blood oxygenation sensors, heart rate monitors, respiration monitors, body contact thermometers. This device works as a portable wireless hub, and can be worn as a watch or pendant. It has built-in GPS functionality to track the location, and medicine/task reminders can be set from a web portal. It automatically detects falls (e.g., by measuring acceleration in three orthogonal dimensions, and can alerts a call center (e.g., by wireless broadband Internet communication) so that immediate help can be provided. In conjunction with other medical devices, this unit can monitor 17 different health parameters, which can be analyzed by a customer or doctor to take precautionary measures (Remote Health Monitoring—mHealth). Red (SOS) and Green (Call Center) buttons can be used to have a 2 way conversation with emergency personnel during an emergency (Mobile Personal Emergency Response System—MPERS). One watch can be used by the entire family by feeding the subscriber id. Doctors can use the watch for code blue, code red and code purple etc.

The devices described above typically communicate information from a single user to another user of an Internet or telephone network connected device, or another one of the watches described above.

There exists a need for a system that can obtain data such as that available from the VESAG brand watch or similar device from a plurality of users in order to provide users with analysis that may be obtained only by processing input from a plurality of sensors worn by individual users.

SUMMARY

One aspect of the disclosure is a body function analysis and communication system including a plurality of wireless communication devices each worn or carried by a respective user and in signal communication with an analysis system. Each wireless communication device is in signal communication with at least one sensor worn by the respective user. The analysis system is configured to determine anomalous response of measurements of the at least one sensor worn by at least one user based on measurements from the plurality of sensors.

A method for analyzing body response of a wearer of a wearable sensor for an anomaly according to another aspect includes wirelessly communicating measurements from at least one sensor worn by each of a plurality of users to an analysis system. The measurements from the at least one sensor worn by each of the plurality of users are analyzed to determine an ordinary body response to a selected stimulus. An abnormal body response from at least one of the worn sensors is determined based on the determined ordinary body response.

Other aspects and advantages will be apparent from the description and claims which follow.

DETAILED DESCRIPTION

Figure 1:
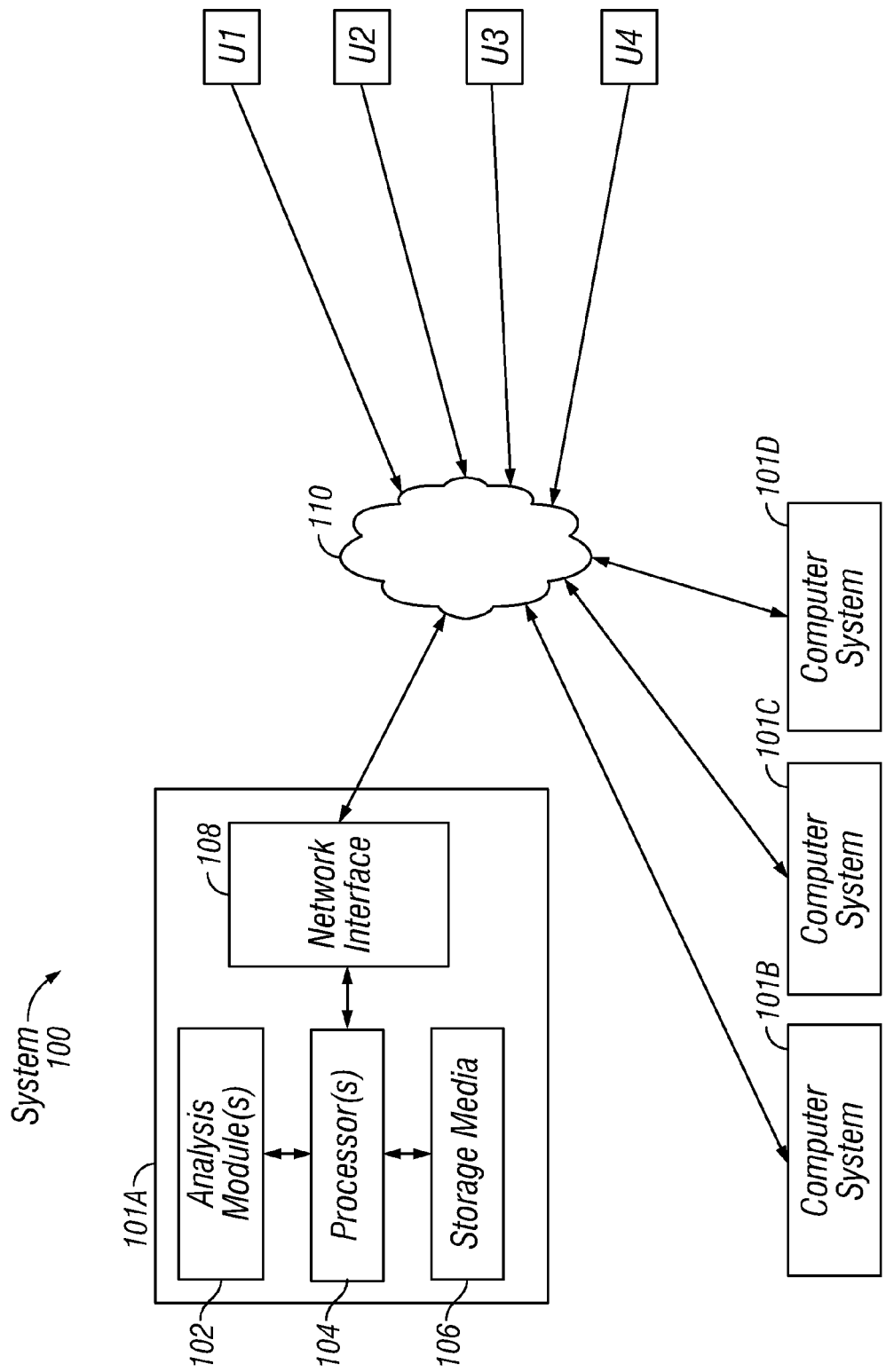
FIG. 1 is a schematic diagram of an example multiple wearable sensor system.

FIG. 1 shows an example data communication and analysis system 100 in accordance with some embodiments. The data communication and analysis system 100 may include an individual computer system 101A or an arrangement of distributed computer systems. The individual computer system 101A may include one or more analysis modules 102 that may be configured to perform various tasks according to some embodiments, such as analysis of data communicated to the data communication and analysis system 100 from a plurality of wearable sensors worn by a plurality of individual users, shown at U1, U2, U3 and U4. Data may be acquired by sensors (not shown separately) worn, e.g., on the body, in some cases in contact with the skin, by the individual users. Non-limiting examples of such sensors may include heart rate monitors, accelerometers, blood oxygenation sensors, respiration rate sensors, skin temperature sensors and skin resistance sensors. The one or more sensors worn on the body by each user U1, U2, U3, U4 may be in wireless signal communication with a wrist-worn device such as the SMARTWATCH device or the VESAG device described in the Background section herein, or a smartphone carried by the user. Sensor signal communication maybe performed using a communication system such as Bluetooth, the protocols and standards for which are managed by the Bluetooth Special Interest Group, Kirkland, Wash.

Signals from the various sensors worn by each user, after communication to the wrist worn device or smartphone, may be in signal communication with the data communication and analysis system 100 using any known wireless communication system or device, e.g., wireless (cellular) Internet communication, shown at 110. Data communicated to the data communication and analysis system 100 from the various users U1, U2, U3, U4 may be stored and analyzed in the data communication and analysis system 100. In one example, data communication and display features may be provided in the wrist worn device similar in configuration to the SMARTWATCH device or VESAG device described in the Background section herein or a smartphone using, e.g., wireless Internet communication as described above. A description of example body worn sensors and communications to various monitoring stations and service providers is described in, S. Patel et al., *A review of wearable sensors and systems with application in rehabilitation*, Journal of NeuroEngineering and Rehabilitation 2012, 9:21.

Figure 2:
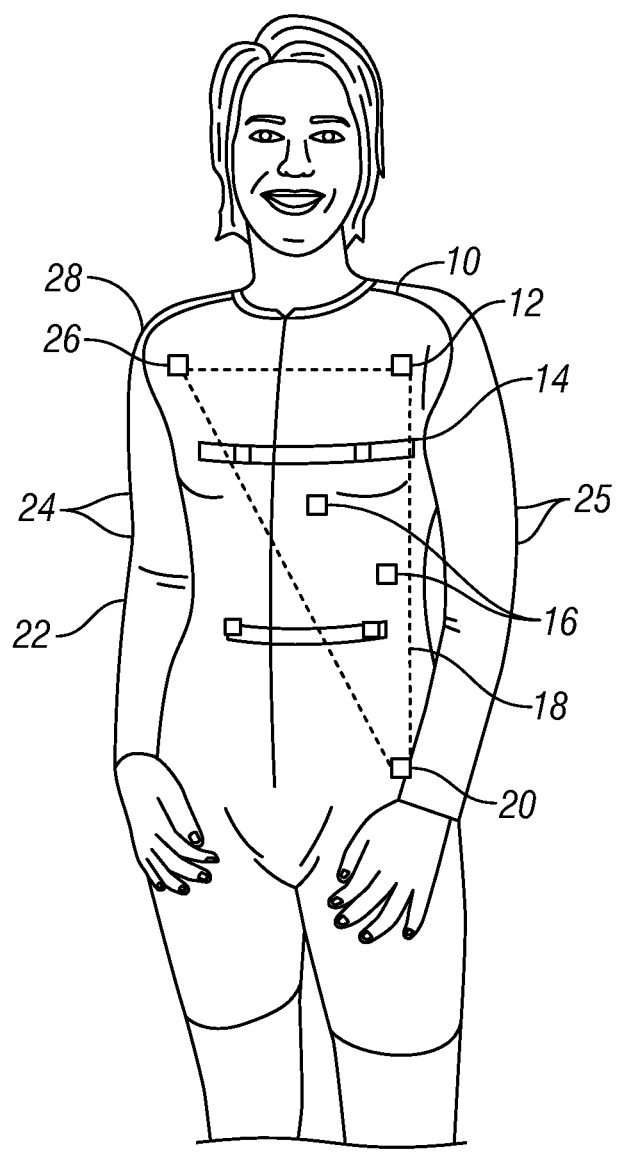
FIG. 2 shows an example set of body-worn sensors that may be used in some embodiments.

Further examples of body-worn sensors are shown schematically in FIG. 2. Examples are shown of an e-textile system 10 for remote, continuous monitoring of physiological and movement data. Embedded sensors provide one with the capability of measuring electrocardiographic data (ECG) 26 using different electrode configurations as well as electromyographic (EMG) 24 and 25 sensor data. Additional sensors allow measuring thoracic 14 and abdominal 18 signals associated with respiration and movement data related to stretching of the garment with shoulder movements 28 and elbow movements 22. Skin temperature may be measured by sensor 12, and skin resistivity may be measured by sensor 20. Precordial leads are shown at 16.

To perform analysis tasks from the data communicated to the data communication and analysis system 100 from the various users U1, U2, U3, U4, an analysis module 102 may execute independently, or in coordination with, one or more processors 104, which may be connected to one or more storage media 106. The processor(s) 104 may also be connected to a network interface 108 to allow the computer system 101A to communicate over the communication device 110 with one or more additional computer systems and/or computing systems, such as 101B, 101C, and/or 101D (note that computer systems 101B, 101C and/or 101D may or may not share the same architecture as computer system 101A, and may be located in different physical locations, for example, computer systems 101A and 101B may be in one physical location, while in communication with one or more computer systems such as 101C and/or 101D that may be located in one or more different locations, e.g., on shore, aboard ships, and/or located in varying countries on different continents.

A "processor" for purposes of the present disclosure may include a microprocessor, microcontroller, processor module or subsystem, programmable integrated circuit, programmable gate array, or another control or computing device.

The storage media 106 may be implemented as one or more computer-readable or machine-readable storage media. Note that while in the embodiment of FIG. 1 the storage media 106 are depicted as within computer system 101A, in some embodiments, the storage media 106 may be distributed within and/or across multiple internal and/or external enclosures of computing system 101A and/or additional computing systems. Storage media 106 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above may be provided on one computer-readable or machine-readable storage medium, or alternatively, can be provided on multiple computer-readable or machine-readable storage media distributed in a large system having possibly plural nodes. Such computer-readable or machine-readable storage medium or media may be considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution, e.g., by wireless or wired Internet communication protocol and hardware.

It should be appreciated that data communication and analysis system 100 is only one example of a computing system, and that the data communication and analysis system 100 may have more or fewer components than shown, may combine additional components not depicted in the example embodiment of FIG. 1, and/or the data communication and analysis system 100 may have a different configuration or arrangement of the components depicted in FIG. 1. The various components shown in FIG. 1 may be implemented in hardware, software, or a combination of both hardware and software, including one or more signal processing and/or application specific integrated circuits.

Further, the steps in an example processing method may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of the present disclosure.

As data are communicated to the data communication and analysis system 100 from the users U1, U2, U3, U4, the data communication and analysis system 100 may perform various analytic functions based on the data input from the plurality of users. Non limiting examples of the foregoing may include acceleration data from a plurality of users within a particular geographic area simultaneously displaying acceleration characteristics (separable from the acceleration of movement of the individual users) indicative of ground motion, such as that associated with an earthquake or impending earthquake. Identification of ground motion may be performed, for example, by analysis of accelerometer signals from a plurality of users and detecting a same acceleration time series or frequency/phase spectrum in the acceleration signals from the plurality of users, e.g., within a determinable geographic area. In such examples, the data communication and analysis system 100 may be programmed to communicate a warning of the condition (e.g. ground motion indicative of an impending earthquake) calculated to the users in the determined affected geographic area.

Another example may be for a plurality of users' within a determinable geographic area have their respective wrist worn or smartphone devices communicate that measurements of blood oxygenation from the respective sensors has changed materially for the affected plurality of affected users. Such may be associated, for example, with leaks of toxic chemicals, and the data communication and analysis system 100 may communicate warnings to the affected users. A similar analysis may be performed, for example, by monitoring heart rate of a plurality of substantially stationary users to determine heart rate changes not resulting from exertion, or if the users are not stationary, using measurements normalized for the degree of exertion which may be inferred from the acceleration measurements. Such users within a determinable geographic area may be subjected to similar hazards such as leaks of toxic chemicals.

Because data for a plurality of users may be stored in the various storage media described above, it may also be possible to generate correlations of normal body responses to certain activities or selected stimuli. For example, measurement of acceleration corresponding to running at determinable speeds (as maybe inferred from the acceleration measurements) and for certain lengths of time, or other physical activity, may be correlated with changes in heart rate, respiration rate, skin temperature and/or electrical resistance and blood oxygenation as measured by the body-worn sensors and communicated to the wrist worn device or smartphone. Such correlation may be performed for a plurality of users to as to establish what may be defined as a "normal" body response to the particular physical activity. Certain users may have physical conditions that result in abnormal body response, which will be detected by those users' body-worn sensors and communicated to the data communication and analysis system as explained above. Abnormal body response may be determined by a particular user's measured heat rate, respiration rate, skin temperature and/or electrical resistivity and blood oxygenation with respect to measurements of acceleration deviating from the determined normal body response by a selected threshold amount. If any such user is determined to exhibit a body response that may be considered to create a health risk, e.g., the abnormal body response deviating from the determined normal body response by a selected threshold amount, a warning signal may be generated by the data communication and analysis system 100 and communicated over the communication system 110 to the affected user(s) (e.g., any of U1 through U4 in FIG. 1). Another example may be the sudden occurrence of an emergency situation, such as a fire, robbery or other traumatic event that may be witnessed by a plurality of users in a particular geographic area. Example body responses to such events may include increase in heart rate, skin resistivity and/or changes in respiration rate. Indications of such body responses that also do not include changes in body motion (e.g., as measured by the accelerometers) may result in the data communication and analysis module 100 communicating a warning message to appropriate response personnel, e.g., firefighters or police. The response personnel may, in some examples, use one or more of the computing systems 101B, 101C, 101D in signal communication with the analysis module 101A. In the foregoing example, if the wrist worn device provides for voice communication, or the user device is a smartphone, the contacted response personnel may initiate a voice communication to any or all of the affected users to verbally confirm the existence of the emergency situation. Further, examples of the warning indicator may include any or all of synthesized voice messages sent to the affected user(s) by a telephone number associated with the wrist work device or smartpone, an SMS text message or an e-mail message sent to the such device(s).

The foregoing are only intended as representative examples or measurement of body parameters of multiple users and possible responses after analysis in the data communication and analysis system 100. It should also be understood that the number of users shown in FIG. 1 is only provided to illustrate the principle of a monitoring and analysis system according to the present disclosure and is not intended to limit the number of users having wearable sensing devices in communication with the data communication and analysis system 100.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A body function analysis and communication system, comprising:
    a plurality of wireless communication devices each worn or carried by a respective user and in signal communication with an analysis system, each wireless communication device in signal communication with at least one sensor worn by the respective user; and
    wherein the analysis system is configured to determine abnormal response of measurements of the at least one sensor worn by at least one user based on a determined normal response calculated by correlating substantially simultaneous measurements from a sensor worn by a plurality of other users that measure a same physical parameter as the sensor worn by the at least one user;
    wherein a threshold for an abnormal response is selected based on the correlation.

2. The system of claim 1 wherein the at least one sensor is configured to communicate with the wireless communication device using Bluetooth communication.

3. The system of claim 1 wherein the at least one sensor comprises at least one of a heart rate sensor, an accelerometer, a skin resistivity sensor, a skin temperature sensor, a respiration rate sensor and a blood oxygenation sensor.

4. A method for analyzing body response of a wearer of a wearable sensor for an anomaly, comprising:
    wirelessly communicating measurements from at least one sensor worn by each of a plurality of users to an analysis system;
    analyzing the measurements from the at least one sensor worn by each of the plurality of users that measure a same physical parameter to determine normal body response to a selected stimulus by correlating substantially simultaneous measurements from each of the sensors; and
    determining an abnormal body response from at least one of the worn sensors based on the determined normal body response, wherein a threshold for an abnormal response is selected based on the correlation.

5. The method of claim 4 further comprising communicating a warning signal to at least one of the wearer of the sensor indicating an anomalous response and an emergency response person.

6. The method of claim 4 wherein the measurements comprise at least one of heart rate, skin temperature and blood oxygenation.

7. The method of claim 4 wherein the determining ordinary body response comprises measurement of acceleration corresponding to running at certain speeds and for certain lengths of time and correlating the measurements of acceleration with at least one of changes in heart rate, respiration rate and blood oxygenation for a plurality of users.

8. The method of claim 7 wherein abnormal body response is determined by measured changes in at least one of changes in heart rate, respiration rate and blood oxygenation with respect to the measured acceleration exceeding a selected threshold difference from changes in heart rate, respiration rate and blood oxygenation with respect to the measured acceleration corresponding to the determined normal body response.

9. The method of claim 4 wherein the measurements comprise acceleration, and wherein the measurements from a plurality of users are analyzed for a time series or frequency/phase spectrum common to the measurements from the plurality of users to identify ground motion within a determinable geographic area.

10. The method of claim 4 wherein the warning signal comprises at least one of a synthesized voice message, an electronic mail message and an SMS text message.

\* \* \* \* \*